US005693675A

United States Patent [19]

Mandeville, III et al.

[11] Patent Number: 5,693,675
[45] Date of Patent: Dec. 2, 1997

[54] ALKYLATED AMINE POLYMERS

[75] Inventors: W. Harry Mandeville, III, Lynnfield; Stephen Randall Holmes-Farley, Arlington, both of Mass.

[73] Assignee: GelTex Pharmaceuticals Inc., Waltham, Mass.

[21] Appl. No.: 461,298

[22] Filed: Jun. 5, 1995

Related U.S. Application Data

[63] Continuation-in-part of Ser. No. 258,431, Jun. 10, 1994, abandoned.

[51] Int. Cl.$^6$ .................................................. C08G 65/04
[52] U.S. Cl. .................. 514/742; 525/328.2; 525/359.1; 525/359.3; 525/359.5; 525/523; 528/421; 528/422
[58] Field of Search .................. 514/742; 525/328.2, 525/523, 359.5, 359.3, 359.1; 528/421, 422

[56] References Cited

U.S. PATENT DOCUMENTS

| | | | |
|---|---|---|---|
| 3,288,770 | 11/1966 | Butler | 260/88.3 |
| 3,308,020 | 3/1967 | Wolf et al. | 167/65 |
| 3,383,281 | 5/1968 | Wolf et al. | 167/65 |
| 3,692,895 | 9/1972 | Nelson et al. | 424/78 |
| 3,780,171 | 12/1973 | Irnscher et al. | 424/79 |
| 3,787,474 | 1/1974 | Daniels et al. | 260/459 |
| 3,803,237 | 4/1974 | Lednicer et al. | 260/584 R |
| 3,980,770 | 9/1976 | Ingelman et al. | 424/79 |
| 4,027,009 | 5/1977 | Grier et al. | 424/78 |
| 4,071,478 | 1/1978 | Shen et al. | 260/2 R |
| 4,098,726 | 7/1978 | Wagner et al. | 528/403 |
| 4,101,461 | 7/1978 | Strop et al. | 521/32 |
| 4,111,859 | 9/1978 | Strop et al. | 521/33 |
| 4,205,064 | 5/1980 | Wagner et al. | 424/78 |
| 4,217,429 | 8/1980 | Wagner et al. | 525/411 |
| 4,340,585 | 7/1982 | Borzatta et al. | 424/79 |
| 4,540,760 | 9/1985 | Harada et al. | 526/211 |
| 4,557,930 | 12/1985 | Kihara et al. | 424/79 |
| 4,559,391 | 12/1985 | Ueda et al. | 525/366 |
| 4,605,701 | 8/1986 | Harada et al. | 525/107 |
| 4,680,360 | 7/1987 | Ueda et al. | 526/310 |
| 4,759,923 | 7/1988 | Buntin et al. | 424/440 |
| 5,055,197 | 10/1991 | Albright et al. | 210/638 |
| 5,142,019 | 8/1992 | Sundararaman et al. | 528/271 |
| 5,236,701 | 8/1993 | St. Pierre et al. | 424/78 |
| 5,300,566 | 4/1994 | Pinschmidt, Jr. et al. | 525/60 |
| 5,374,422 | 12/1994 | St. Pierre et al. | 424/78.12 |
| 5,395,896 | 3/1995 | Moriya et al. | 525/328.2 |
| 5,414,068 | 5/1995 | Bliem et al. | 528/288 |
| 5,428,112 | 6/1995 | Ahlers et al. | 525/326.7 |
| 5,430,110 | 7/1995 | Ahlers et al. | 525/328.2 |
| 5,451,397 | 9/1995 | Albright et al. | 424/78.01 |

FOREIGN PATENT DOCUMENTS

| | | |
|---|---|---|
| 0 162 388 | 11/1985 | European Pat. Off. . |
| 0432995A1 | 6/1991 | European Pat. Off. . |
| 0580078A1 | 1/1994 | European Pat. Off. . |
| 0580079A1 | 1/1994 | European Pat. Off. . |
| 929391 | 6/1963 | United Kingdom . |
| 1567294 | 5/1980 | United Kingdom . |
| WO91/18027 | 11/1991 | WIPO . |
| WO92/10522 | 6/1992 | WIPO . |
| WO94/04596 | 3/1994 | WIPO . |
| WO94/27620 | 8/1994 | WIPO . |

OTHER PUBLICATIONS

Heming, A.E. and Flanagan, Thomas L., "Considerations in the Selection of Cation Exchange Resins for Therapeutic Use," *Annals of the New York Academy of Sciences*, 57:239-251 (1954).

McCarthy, Peter A., "New Approaches to Atherosclerosis: An Overview," *Medicinal Research Reviews*, 13(2):139-159 (1993).

*Primary Examiner*—Terressa Mosley
*Attorney, Agent, or Firm*—Hamilton, Brook, Smith & Reynolds, P.C.

[57] ABSTRACT

The invention relates to alkylated amine polymers and a method for removing bile salts from a patient that includes administering to the patient a therapeutically effective amount of product produced by a process comprising alkylating one or more crosslinked amine polymers, salts or copolymers thereof with at least one alkylating agent. The reaction product is characterized in that: (i) at least some of the nitrogen atoms are unreacted with alkylating agent; and (ii) less than 10 mol % of the nitrogen atoms in the polymer react with the alkylating agent to form quaternary ammonium units.

38 Claims, No Drawings

ALKYLATED AMINE POLYMERS

RELATED APPLICATION

This application is a continuation-in-part of U.S. Ser. No. 08/258.431 filed Jun. 10, 1994, abandoned the entire teachings of which are incorporated herein by reference.

BACKGROUND OF THE INVENTION

This invention relates to removing bile salts from a patient.

Salts of bile acids act as detergents to solubilize and consequently aid in digestion of dietary fats. Bile acids are precursors to bile salts, and are derived from cholesterol. Following digestion, bile acids can be passively absorbed in the jejunum, or, in the case of conjugated primary bile acids, reabsorbed by active transport in the ileum. Bile acids which are not reabsorbed by active transport are deconjugated and dehydroxylated by bacterial action in the distal ileum and large intestine.

Reabsorption of bile acids from the intestine conserves lipoprotein cholesterol in the bloodstream. Conversely, blood cholesterol level can be diminished by reducing reabsorption of bile acids.

One method of reducing the amount of bile acids that are reabsorbed is oral administration of compounds that sequester the bile acids and cannot themselves be absorbed. The sequestered bile acids consequently either decompose by bacterial action or are excreted.

Many bile acid sequestrants, however, bind relatively hydrophobic bile acids more avidly than conjugated primary bile acids, such as conjugated cholic and chenodeoxycholic acids. Further, active transport in the ileum causes substantial portions of sequestered conjugated primary bile acids to be desorbed and to enter the free bile acid pool for reabsorption. In addition, the volume of sequestrants that can be ingested safely is limited. As a result, the effectiveness of sequestrants to diminish blood cholesterol levels is also limited.

Sequestering and removing bile salts (e.g., cholate, glycocholate, glycochenocholate, taurocholate, and deoxycholate salts) in a patient can be used to reduce the patient's cholesterol level. Because the biological precursor to bile salt is cholesterol, the metabolism of cholesterol to make bile salts is accompanied by a simultaneous reduction in the cholesterol in the patient.

Cholestyramine, a polystyrene/divinylbenzene ammonium ion exchange resin, when ingested, removes bile salts via the digestive tract. This resin, however, is unpalatable, gritty and constipating. Resins which avoid (totally or partially) these disadvantages and/or possess improved bile salt sequestration properties are needed.

SUMMARY OF THE INVENTION

The invention relates to the discovery that a new class of ion exchange resins have improved bile salt sequestration properties and little to no grittiness, thereby improving the palatability of the composition.

The resins comprise cross-linked polyamines which are characterized by one or more hydrophobic substituents and, optionally, one or more quaternary ammonium containing substituents.

In general, the invention features resins and their use in removing bile salts from a patient that includes administering to the patient a therapeutically effective amount of the reaction product of:

(a) one or more crosslinked polymers, salts and copolymers thereof characterized by a repeat unit selected from the group consisting essentially of:

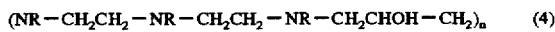

where n is a positive integer and each R, independently, is H or a substituted or unsubstituted alkyl group (e.g., $C_1$–$C_8$ alkyl); and (b) at least one alkylating agent. The reaction product is characterized in that: (i) at least some of the nitrogen atoms in the repeat units are unreacted with the alkylating agent; (ii) less than 10 mol % of the nitrogen atoms in the repeat units that react with the alkylating agent form quaternary ammonium units; and (iii) the reaction product is preferably non-toxic and stable once ingested.

Suitable substituents include quaternary ammonium, amine, alkylamine, dialkylamine, hydroxy, alkoxy, halogen, carboxamide, sulfonamide and carboxylic acid ester, for example.

In preferred embodiments, the polyamine of compound (a) of the reaction product is crosslinked by means of a multifunctional crosslinking agent, the agent being present in an amount from about 0.5–25% (more preferably about 2.5–20% (most preferably 1–10%)) by weight, based upon total weight or monomer plus crosslinking agent. A preferred crosslinking agent is epichlorohydrin because of its high availability and low cost. Epichlorohydrin is also advantageous because of it's low molecular weight and hydrophilic nature, increasing the water-swellability and gel properties of the polyamine.

The invention also features compositions based upon the above-described reaction products.

The invention provides an effective treatment for removing bile salts from a patient (and thereby reducing the patient's cholesterol level). The compositions are non-toxic and stable when ingested in therapeutically effective amounts.

Other features and advantages will be apparent from the following description of the preferred embodiments thereof and from the claims.

DETAILED DESCRIPTION OF THE INVENTION

Compositions

Preferred reaction products include the products of one or more crosslinked polymers having the formulae set forth in the Summary of the Invention, above, and one or more alkylating agents. The polymers are crosslinked. The level of crosslinking makes the polymers completely insoluble and thus limits the activity of the alkylated reaction product to the gastrointestinal tract only. Thus, the compositions are non-systemic in their activity and will lead to reduced side-effects in the patient.

By "non-toxic" it is meant that when ingested in therapeutically effective amounts neither the reaction products nor any ions released into the body upon ion exchange are harmful. Cross-linking the polymer renders the polymer substantially resistant to absorption. When the polymer is administered as a salt, the cationic counterions are preferably selected to minimize adverse effects on the patient, as is more particularly described below.

By "stable" it is meant that when ingested in therapeutically effective amounts the reaction products do not dissolve or otherwise decompose in vivo to form potentially harmful by-products, and remain substantially intact so that they can transport material out of the body.

By "salt" it is meant that the nitrogen group in the repeat unit is protonated to create a positively charged nitrogen atom associated with a negatively charged counterion.

By "alkylating agent" it is meant a reactant which, when reacted with the crosslinked polymer, causes an alkyl group or derivative thereof (e.g., a substituted alkyl, such as an aralkyl, hydroxyalkyl, alkylammonium salt, alkylamide, or combination thereof) to be covalently bound to one or more of the nitrogen atoms of the polymer.

One example of preferred polymer is characterized by a repeat unit having the formula

(5)

or a salt or copolymer thereof; wherein x is zero or an integer between about 1 to 4.

A second example of a preferred polymer is characterized by a repeat unit having the formula

(6)

or a salt or copolymer thereof.

A third example of a preferred polymer is characterized by a repeat unit having the formula

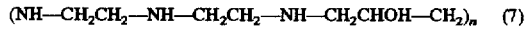

(7)

or a salt or copolymer thereof.

The polymers are preferably crosslinked prior to alkylation. Examples of suitable crosslinking agents include acryloyl chloride, epichlorohydrin, butanedioldiglycidyl ether, ethanedioldiglycidyl ether, and dimethyl succinate. The amount of crosslinking agent is typically between 0.5 and 25 weight %, based upon combined weight of crosslinking agent and monomer, with 2.5–20%, or 1–10%, being preferred.

Typically, the amount of crosslinking agent that is reacted with the amine polymer is sufficient to cause between about 0.5 and twenty percent of the amines. In a preferred embodiment, between about 0.5 and six percent of the amine groups react with the crosslinking agent.

Crosslinking of the polymer can be achieved by reacting the polymer with a suitable crosslinking agent in an aqueous caustic solution at about 25° C. for a period of time of about eighteen hours to thereby form a gel. The gel is then combined with water and blended to form a particulate solid. The particulate solid can then be washed with water and dried under suitable conditions, such as a temperature of about 50° C. for a period of time of about eighteen hours.

Alkylation involves reaction between the nitrogen atoms of the polymer and the alkylating agent (which may contain additional nitrogen atoms, e.g., in the form of amido or ammonium groups). In addition, the nitrogen atoms which do react with the alkylating agent(s) resist multiple alkylation to form quaternary ammonium ions such that less than 10 mol % of the nitrogen atoms form quaternary ammonium ions at the conclusion of alkylation.

Preferred alkylating agents have the formula RX where R is a $C_1$–$C_{20}$ alkyl (preferably $C_4$–$C_{20}$), $C_1$–$C_{20}$ hydroxyalkyl (preferably $C_4$–$C_{20}$ hydroxyalkyl), $C_7$–$C_{20}$ aralkyl, $C_1$–$C_{20}$ alkylammonium (preferably $C_4$–$C_{20}$ alkyl ammonium), or $C_1$–$C_{20}$ alkylamido (preferably $C_4$–$C_{20}$ alkyl amido) group and X includes one or more electrophilic leaving groups. By "electrophilic leaving group" it is meant a group which is displaced by a nitrogen atom in the crosslinked polymer during the alkylation reaction. Examples of preferred leaving groups include halide, epoxy, rosylate, and mesylate group. In the case of, e.g., epoxy groups, the alkylation reaction causes opening of the three-membered epoxy ring.

Examples of preferred alkylating agents include a $C_1$–$C_{20}$ alkyl halide (e.g., an n-butyl halide, n-hexyl halide, n-octyl halide, n-decyl halide, n-dodecyl halide, n-tetradecyl halide, n-octadecyl halide, and combinations thereof); a $C_1$–$C_{20}$ dihaloalkane (e.g., a 1,10-dihalodecane); a $C_1$–$C_{20}$ hydroxyalkyl halide (e.g., an 11-halo-1-undecanol); a $C_1$–$C_{20}$ aralkyl halide (e.g., a benzyl halide); a $C_1$–$C_{20}$ alkyl halide ammonium salt (e.g., a (4-halobutyl) trimethylammonium salt, (6-halohexyl)trimethylammonium salt, (8-halooctyl) trimethylammonium salt, (10-halodecyl) trimethylammonium salt, (12-halododecyl) trimethylammonium salts and combinations thereof); a $C_1$–$C_{20}$ alkyl epoxy ammonium salt (e.g., a (glycidylpropyl) trimethylammonium salt); and a $C_1$–$C_{20}$ epoxy alkylamide (e.g., an N-(2,3-eoxypropane)butyramide, N-(2,3-epoxypropane)hexanamide, and combinations thereof).

It is particularly preferred to react the polymer with at least two alkylating agents, added simultaneously or sequentially to the polymer. In one preferred example, one of the alkylating agents has the formula RX where R is a $C_1$–$C_{20}$ alkyl group and X includes one or more electrophilic leaving groups (e.g., an alkyl halide), and the other alkylating agent has the formula R'X where R' is a $C_1$–$C_{20}$ alkyl ammonium group and X includes one or more electrophilic leaving groups (e.g., an alkyl halide ammonium salt).

In another preferred example, one of the alkylating agents has the formula RX where R is a $C_1$–$C_{20}$ alkyl group and X includes one or more electrophilic leaving groups (e.g., an alkyl halide), and the other alkylating agent has the formula R'X where R' is a $C_1$–$C_{20}$ hydroxyalkyl group and X includes one or more electrophilic leaving groups (e.g., a hydroxy alkyl halide).

In another preferred example, one of the alkylating agents is a $C_1$–$C_{20}$ dihaloalkane and the other alkylating agent is a $C_1$–$C_{20}$ alkylammonium salt.

The reaction products may have fixed positive charges, or may have the capability of becoming charged upon ingestion at physiological pH. In the latter case, the charged ions also pick up negatively charged counterions upon ingestion that can be exchanged with bile salts. In the case of reaction products having fixed positive charges, however, the reaction product may be provided with one or more exchangeable counterions. Examples of suitable counterions include $Cl^-$, $Br^-$, $CH_3OSO_3^-$, $HSO_4^-$, $SO_4^{2-}$, $HCO_3^-$, $CO_3^-$, acetate, lactate, succinate, propionate, butyrate, ascorbate, citrate, maleate, folate, an amino acid derivative, a nucleotide, a lipid, or a phospholipid. The counterions may be the same as, or different from, each other. For example, the reaction product may contain two different types of counterions, both of which are exchanged for the bile salts being removed. More than one reaction product, each having different counterions associated with the fixed charges, may be administered as well.

The alkylating agent can be added to the cross-linked polymer at a molar ratio between about 0.05:1 to 4:1, for example, the alkylating agents can be preferably selected to provide hydrophobic regions and hydrophilic regions.

The amine polymer is typically alkylated by combining the polymer with the alkylating agents in an organic solvent. The amount of first alkylating agent combined with the amine polymer is generally sufficient to cause reaction of the first alkylating agent with between about 5 and 75 of the percent of amine groups on the amine polymer that are available for reaction. The amount of second alkylating agent combined with the amine polymer and solution is generally sufficient to cause reaction of the second alkylating agent with between about 5 and about 75 of the amine groups available for reaction on the amine polymer. Examples of suitable organic solvents include methanol, ethanal, isopropanol, acetonitrile, DMF and DMSO. A preferred organic solvent is methanol.

In one embodiment, the reaction mixture is heated over a period of about forty minutes to a temperature of about 65° C., with stirring. Typically, an aqueous sodium hydroxide solution is continuously added during the reaction period. Preferably, the reaction period at 65° C. is about eighteen hours, followed by gradual cooling to a room temperature of about 25° C. over a period of about four hours. The resulting reaction product is then filtered, resuspended in methanol, filtered again, and then washed with a suitable aqueous solution, such as two molar sodium chloride, and then with deionized water. The resultant solid product is then dried under suitable conditions, such as at a temperature of about 60° C. in an air-drying oven. The dried solid can then be subsequently processed. Preferably, the solid is ground and passed through an 80 mesh sieve.

In a particularly preferred embodiment of the invention, the amine polymer is a crosslinked poly(allylamine), wherein the first substituent includes a hydrophobic decyl moiety, and the second amine substituent includes a hexyltrimethylammonium. Further, the particularly preferred crosslinked poly(allylamine) is crosslinked by epichlorohydrin that is present in a range of between about two and six percent of the amines available for reaction with the epichlorohydrin.

The invention will now be described more specifically by the examples.

EXAMPLES

A. Polymer Preparation
1. Preparation of Poly (vinylamine)

The first step involved the preparation of ethylidenebisacetamide. Acetamide (118 g), acetaldehyde (44.06 g), copper acetate (0.2 g), and water (300 mL) were placed in a 1 L three neck flask fitted with condenser, thermometer, and mechanical stirred. Concentrated HCl (34 mL) was added and the mixture was heated to 45°–50° C. with stirring for 24 hours. The water was then removed in vacuo to leave a thick sludge which formed crystals on cooling to 5° C. Acetone (200 mL) was added and stirred for a few minutes, after which the solid was filtered off and discarded. The acetone was cooled to 0° C. and solid was filtered off. This solid was rinsed in 500 mL acetone and air dried 18 hours to yield 31.5 g of ethylidenebisacetamide.

The next step involved the preparation of vinylacetamide from ethylidenebisacetamide. Ethylidenebisacetamide (31.05 g), calcium carbonate (2 g) and celite 541 (2 g) were placed in a 500 mL three neck flask fitted with a thermometer, a mechanical stirred, and a distilling heat atop a Vigroux column. The mixture was vacuum distilled at 24 mm Hg by heating the pot to 180°–225° C. Only a single fraction was collected (10.8 g) which contained a large portion of acetamide in addition to the product (determined by NMR). This solid product was dissolved in isopropanol (30 mL) to form the crude vinylacetamide solution used for polymerization.

Crude vinylacetamide solution (15 mL), divinylbenzene (1 g, technical grade, 55% pure, mixed isomers), and AIBN (0.3 g) were mixed and heated to reflux under a nitrogen atmosphere for 90 minutes, forming a solid precipitate. The solution was cooled, isopropanol (50 mL) was added, and the solid was collected by centrifugation. The solid was rinsed twice in isopropanol, once in water, and dried in a vacuum oven to yield 0.8 g of poly(vinylacetamide), which was used to prepare poly(vinylamine as follows).

Poly(vinylacetamide) (0.79 g) was placed in a 100 mL one neck flask containing water (25 mL) and conc. HCl (25 mL). The mixture was refluxed for 5 days, after which the solid was filtered off, rinsed once in water, twice in isopropanol, and dried in a vacuum oven to yield 0.77 g of product. Infrared spectroscopy indicated that a significant amount of the amide (1656 $cm^{-1}$) remained and that not much amine 91606 $cm^{-1}$) was formed. The product of this reaction (~0.84 g) was suspended in NaOh (46 g) and water (46 g) and heated to boiling (~140° C.). Due to foaming the temperature was reduced and maintained at ~100° C. for 2 hours. Water (100 mL) was added and the solid collected by filtration. After rinsing once in water the solid was suspended in water (500 mL) and adjusted to pH 5 with acetic acid. The solid was again filtered off, rinsed with water, then isopropanol, and dried in a vacuum oven to yield 0.51 g of product. Infrared spectroscopy indicated that significant amine had been formed.

2. Preparation of Poly(ethyleneimine)

Polyethyleneimine (120 g of a 50% aqueous solution; Scientific Polymer Products) was dissolved in water (250 mL). Epichlorohydrin (22.1 mL) was added dropwise. The solution was heated to 60° C. for 4 hours, after which it had gelled. The gel was removed, blended with water (1.5 L) and the solid was filtered off, rinsed three times with water (3 L) and twice with isopropanol (3 L), and the resulting gel was dried in a vacuum oven to yield 81.2 g of the title polymer.

3. Preparation of Poly(allylamine) hydrochloride

To a 2 liter, water-jacketed reaction kettle equipped with (1) a condenser topped with a nitrogen gas inlet, 92) a thermometer, and (3) a mechanical stirrer was added concentrated hydrochloric acid (360 mL). The acid was cooled to 5° C. using circulating water in the jacket of the reaction kettle (water temperature=0° C.). Allylamine (328.5 mL, 250 g) was added dropwise with stirring while maintaining the reaction temperature at 5°–10° C. After addition was complete, the mixture was removed, placed in a 3 liter one-neck flask, and 206 g of liquid was removed by rotary vacuum evaporation at 60° C. Water (20 mL) was then added and the liquid was returned to the reaction kettle. Azobis (amidinopropane) dihydrochloride (0.5 g) suspended in 11 mL of water was then added. The resulting reaction mixture was heated to 50° C. under a nitrogen atmosphere with stirring for 24 hours. Additional azobis(amidinopropane) dihydrochloride (5 mL) suspended in 11 mL of water was then added, after which heating and stirring were continued for an additional 44 hours.

At the end of this period, distilled water (100 mL) was added to the reaction mixture and the liquid mixture allowed to cool with stirring. The mixture was then removed and placed in a 2 liter separatory funnel, after which it was added dropwise to a stirring solution of methanol (4 L), causing a solid to form. The solid was removed by filtration, re-suspended in methanol (4 L), stirred for 1 hour, and collected by filtration. The methanol rinse was then repeated one more time and the solid dried in a vacuum oven to afford 215.1 g of poly(allylamine) hydrochloride as a granular white solid.

4. Preparation of Poly(allylamine) hydrochloride crosslinked with epichlorohydrin To a 5 gallon vessel was added poly(allylamine) hydrochloride prepared as described in Example 3 (1 kg) and water (4 L). The mixture was stirred to dissolve the hydrochloride and the pH was adjusted by adding solid NaOH (284 g). The resulting solution was cooled to room temperature, after which epichlorohydrin crosslinking agent (50 mL) was added all at once with stirring. The resulting mixture was stirred gently until it gelled (about 35 minutes). The crosslinking reaction was allowed to proceed for an additional 18 hours at room temperature, after which the polymer gel was removed and placed in portions in a blender with a total of 10 L of water. Each portion was blended gently for about 3 minutes to form coarse particles which were then stirred for 1 hour and collected by filtration. The solid was rinsed three times by suspending it in water (10 L, 15 L, 20 L), stirring each suspension for 1 hour, and collecting the solid each time by filtration. The resulting solid was then rinsed once by suspending it in isopropanol (17 L), stirring the mixture for 1 hour, and then collecting the solid by filtration, after which the solid was dried in a vacuum oven at 50° C. for 18 hours to yield about 677 g of the cross linked polymer as a granular, brittle, white solid.

5. Preparation of Poly(allylamine) hydrochloride crosslinked with butanedioldiglycidyl ether To a 5 gallon plastic bucket was added poly(allylamine) hydrochloride prepared as described in Example 3 (500 g) and water (2 L). The mixture was stirred to dissolve the hydrochloride and the pH was adjusted to 10 by adding solid NaOH (134.6 g). The resulting solution was cooled to room temperature in the bucket, after which 1,4-butanedioldiglycidyl ether crosslinking agent (65 mL) was added all at once with stirring. The resulting mixture was stirred gently until it gelled (about 6 minutes). The crosslinking reaction was allowed to proceed for an additional 18 hours at room temperature, after which the polymer gel was removed and dried in a vacuum oven at 75° C. for 24 hours. The dry solid was then ground and sieved to −30 mesh, after which it was suspended in 6 gallons of water and stirred for 1 hour. The solid was then filtered off and the rinse process repeated two more times. The resulting solid was then air dried for 48 hours, followed by drying in a vacuum oven at 50° C. for 24 hours to yield about 415 g of the crosslinked polymer as a white solid.

6. Preparation of Poly(allylamine) hydrochloride crosslinked with ethanedioldiglycidyl ether To a 100 mL beaker was added poly(allylamine) hydrochloride prepared as described in Example 3 (10 g) and water (40 mL). The mixture was stirred to dissolve the hydrochloride and the pH was adjusted to 10 by adding solid NaOH. The resulting solution was cooled to room temperature in the beaker, after which 1,2-ethanedioldiglycidyl ether crosslinking agent (2.0 mL) was added all at once with stirring. The resulting mixture was stirred gently until it gelled (about 4 minutes). The crosslinking reaction was allowed to proceed for an additional 18 hours at room temperature, after which the polymer gel was removed and blended in 500 mL of methanol. The solid was then filtered off and suspended in water (500 mL). After stirring for 1 hour, the solid was filtered off and the rinse process repeated. The resulting solid was rinsed twice in isopropanol (400 mL) and then dried in a vacuum oven at 50° C. for 24 hours to yield 8.7 g of the crosslinked polymer as a white solid.

7. Preparation of Poly(allylamine) hydrochloride crosslinked with dimethylsuccinate To a 500 mL round bottom flask was added poly(allylamine) hydrochloride prepared as described in Example 3 (10 g), methanol (100 mL), and triethylamine (10 mL). The mixture was stirred and dimethylsuccinate crosslinking agent (1 mL) was added. The solution was heated to reflux and the stirring discontinued after 30 minutes. After 18 hours, the solution was cooled to room temperature, and the solid filtered off and blended in 400 mL of isopropanol. The solid was then filtered off and suspended in water (1 L). After stirring for 1 hour, the solid was filtered off and the rinse process repeated two more times. The solid was then rinsed once in isopropanol (800 mL) and dried in a vacuum oven at 50° C. for 24 hours to yield 5.9 g of the crosslinked polymer as a white solid.

8. Preparation of Poly(ethyleneimine) crosslinked with acryloyl chloride

Into a 5 L three neck flask equipped with a mechanical stirred, a thermometer, and an addition funnel was added poly(ethyleneimine) (510 g of a 50% aqueous solution, equivalent to 255 g of dry polymer) and isopropanol (2.5 L). Acryloyl chloride crosslinking agent (50 g) was added dropwise through the addition funnel over a 35 minute period while maintaining the temperature below 29° C. The solution was then heated to 60° C. with stirring for 18 hours, after which the solution was cooled and the solid immediately filtered off. The solid was then washed three times by suspending it in water (2 gallons), stirring for 1 hour, and filtering to recover the solid. Next, the solid was rinsed once by suspending it in methanol (2 gallons), stirring for 30 minutes, and filtering to recover the solid. Finally, the solid was rinsed in isopropanol as in Example 7 and dried in a vacuum oven at 50° C. for 18 hours to yield 206 g of the crosslinked polymer as a light orange granular solid.

9. Alkylation of Poly(allylamine) crosslinked with butanedioldiglydicyl ether with 1-iodooctane alkylating agent Poly(allylamine) crosslinked with butanedioldiglycidyl ether prepared as described in Example 5 (5 g) was suspended in methanol (100 mL) and sodium hydroxide (0.2 g) was added. After stirring for 15 minutes, 1-iodooctane (1.92 mL) was added and the mixture stirred at 60° C. for 20 hours. The mixture was then cooled and the solid filtered off. Next, the solid was washed by suspending it in isopropanol (500 mL), after which it was stirred for 1 hour and then collected by filtration. The wash procedure was then repeated twice using aqueous sodium chloride (500 mL of a 1M solution), twice with water (500 mL), and once with isopropanol (500 mL) before drying in a vacuum oven at 50° C. for 24 hours to yield 4.65 g of alkylated product.

The procedure was repeated using 2.88 mL of 1-iodooctane to yield 4.68 g of alkylated product.

10. Alkylation of Poly(allylamine) crosslinked with epichlorohydrin with 1-iodooctane alkylating agent Poly(allylamine) crosslinked with epichlorohydrin prepared as described in Example 4 (5 g) was alkylated according to the procedure described in Example 9 except that 3.84 mL of 1-iodooctane was used. The procedure yielded 5.94 g of alkylated product.

11. Alkylation of Poly(allylamine) crosslinked with epichlorohydrin with 1-iodooctadecane alkylating agent Poly(allylamine) crosslinked with epichlorohydrin prepared as described in Example 4 (10 g) was suspended in methanol (100 mL) and sodium hydroxide (0.2 g) was added. After stirring for 15 minutes, 1-iodooctadecane (8.1 g) was added and the mixture stirred at 60° C. for 20 hours. The mixture was then cooled and the solid filtered off. Next, the solid was washed by suspending it in isopropanol (500 mL), after which it was stirred for 1 hour and then collected by filtration. The wash procedure was then repeated twice using aqueous sodium chloride (500 mL of a 1M solution), twice with water (500 mL), and once with isopropanol (500 mL) before drying in a vacuum oven at 50° C. for 24 hours to yield 9.6 g of alkylated product.

12. Alkylation of Poly(allylamine) crosslinked with butanedioldiglycidyl ether with 1-iodododecane alkylating agent Poly(allylamine) crosslinked with butanedioldiglycidyl ether prepared as described in Example 5 (5 g) was alkylated according to the procedure described in Example 11 except that 2.47 mL of 1-iodododecane was used. The procedure yielded 4.7 g of alkylated product.

13. Alkylation of Poly(allylamine) crosslinked with butanedioldiglycidyl ether with benzyl bromide alkylating agent Poly(allylamine) crosslinked with butanedioldiglycidyl ether prepared as described in Example 5 (5 g) was alkylated according to the procedure described in Example 11 except that 2.42 mL of benzyl bromide was used. The procedure yielded 6.4 g of alkylated product.

14. Alkylation of Poly(allylamine) crosslinked with epichlorohydrin with benzyl bromide alkylating agent Poly(allylamine) crosslinked with epichlorohydrin prepared as described in Example 4 (5 g) was alkylated according to the procedure described in Example 11 except that 1.21 mL of benzyl bromide was used. The procedure yielded 6.6 g of alkylated product.

15. Alkylation of Poly(allylamine) crosslinked with epichlorohydrin with 1-iododdecane alkylating agent Poly(allylamine) crosslinked with epichlorohydrin prepared as described in Example 4 (20 g) was alkylated according to the procedure described in Example 11 except that 7.15 g of 1-iododecane and 2.1 g of NaOH were used. The procedure yielded 20.67 g of alkylated product.

16. Alkylation of Poly(allylamine) crosslinked with epichlorohydrin with 1-iodobutane alkylating agent Poly(allylamine) crosslinked with epichlorohydrin prepared as described in Example 4 (20 g) was alkylated according to the procedure described in Example 11 except that 22.03 g of 1-iodobutane and 8.0 g of NaOH were used. The procedure yielded 24.0 g of alkylated product.

The procedure was also followed using 29.44 g and 14.72 g of 1-iodobutane to yield 17.0 g and 21.0 g, respectively, of alkylated product.

17. Alkylation of Poly(allylamine) crosslinked with epichlorohydrin with 1-iodotetradecane alkylating agent Poly(allylamine) crosslinked with epichlorohydrin prepared as described in Example 4 (5 g) was alkylated according to the procedure described in Example 11 except that 2.1 mL of 1-iodotetradecane was used. The procedure yielded 5.2 g of alkylated product.

The procedure was also followed using 6.4 mL of 1-iodotetradecane to yield 7.15 g of alkylated product.

18. Alkylation of Poly(allylamine) crosslinked with epichlorohydrin with 1-iodooctane alkylating agent Poly(allylamine) crosslinked with epichlorohydrin prepared as described in Example 8 (5 g) was alkylated according to the procedure described in Example 11 except that 1.92 mL of 1-iodooctane was used. The procedure yielded 5.0 g of alkylated product.

19. Alkylation of a Copolymer of diethylene triamine and epichlorohydrin with 1-iodooctane alkylating agent A copolymer of diethylene triamine and epichlorohydrin (10 g) was alkylated according to the procedure described in Example 11 except that 1.92 mL of 1-iodooctane was used. The procedure yielded 5.3 g of alkylated product.

20. Alkylation of Poly(allylamine) crosslinked with epichlorohydrin with 1-iodododecane and glycidylpropyltrimethylammonium chloride alkylating agents Poly(allylamine) crosslinked with epichlorohydrin prepared as described in Example 4 (20 g) was alkylated according to the procedure described in Example 11 except that 23.66 g of 1-iodododecane, 6.4 g of sodium hydroxide, and 500 mL of methanol were used. 24 grams of the alkylated product was then reacted with 50 g of 90% glycidylpropyltrimethylammonium chloride in methanol (1 L). The mixture was stirred at reflux for 24 hours, after which it was cooled to room temperature and washed successively with water (three times using 2.5 L each time). Vacuum drying afforded 22.4 g of dialkylated product.

Dialkylated products were prepared in an analogous manner by replacing 1-iodododecane with 1-iododecane and 1-iodooctadecane, respectively, followed by alkylation with glycidylpropyltrimethylammonium chloride.

21. Alkylation of Poly(allylamine) crosslinked with epichlorohydrin with glycidylpropyltrimethylammonium chloride alkylating agent Poly(allylamine) crosslinked with epichlorohydrin prepared as described in Example 4 (5 g) was reacted with 11.63 g of 90% glycidylpropyltrimethylammonium chloride (1 mole equiv.) in methanol (100 mL). The mixture was stirred at 60° C. for 20 hours, after which it was cooled to room temperature and washed successively with water (three times using 400 mL each time) and isopropanol (one time using 400 mL). Vacuum drying afforded 6.93 g of alkylated product.

Alkylated products were prepared in an analogous manner using 50%, 200%, and 300% mole equiv of 90% glycidylpropyltrimethylammonium chloride.

22. Alkylation of Poly(allylamine) crosslinked with epichlorohydrin with (10-bromodecyl)trimethylammonium bromide alkylating agent The first step is the preparation of (10-bromodecyl) trimethylammonium bromide as follows.

1,10-dibromodecane (200 g) was dissolved in methanol (3 L) in a 5 liter three neck round bottom flask fitted with a cold condenser (−5° C.). To this mixture was added aqueous trimethylamine (176 mL of a 24% aqueous solution, w/w). The mixture was stirred at room temperature for 4 hours, after which is was heated to reflux for an additional 18 hours. At the conclusion of the heating period, the flask was cooled to 50° C. and the solvent removed under vacuum to leave a solid mass. Acetone (300 mL) was added and the mixture stirred at 40° C. for 1 hour. The solid was filtered off, resuspended in an additional portion of acetone (1 L), and stirred for 90 minutes.

At the conclusion of the stirring period, the solid was filtered and discarded, and the acetone fractions were combined and evaporated to dryness under vacuum. Hexanes (about 1.5 L) were added and the mixture then stirred for 1 hour, after which the solid was filtered off and then rinsed on the filtration funnel with fresh hexanes. The resulting solid was then dissolved in isopropanol (75 mL) at 40° C. Ethyl acetate (1500 mL) was added and the temperature raised to about 50° C. to fully dissolve all solid material. The flask was then wrapped in towels and placed in a freezer for 24 hours, resulting in the formation of solid crystals. The crystals were filtered off, rinsed in cold ethyl acetate, and dried in a vacuum oven at 75° C. to yield 100.9 g of (10-bromodecyl) trimethylammonium bromide as white crystals.

Poly(allylamine) crosslinked with epichlorohydrin prepared as described in Example 4 (10 g) was suspended in methanol (300 mL). Sodium hydroxide (3.3 g) was added and the mixture stirred until it dissolved. (10-bromodecyl) trimethylammonium bromide (20.7 g) was added and the mixture was refluxed with stirring for 20 hours. The mixture was then cooled to room temperature and washed successively with methanol (two times using 1 L each time), sodium chloride) two times using 1 L of 1M solution each time), water (three times using 1 L each time), and isopropanol (one time using 1 L). Vacuum drying yielded 14.3 g of alkylated product.

23. Alkylation of Poly(allylamine) crosslinked with epichlorohydrin with (10-bromodecyl)trimethylammonium bromide and 1,10-dibromodecane alkylating agents 1,10-dibromodecane (200 g) was dissolved in methanol (3 L) in a 5 liter round bottom flask fitted with a cold condenser (−5° C.). To this mixture was added aqueous trimethylamine (220 mL of a 24% aqueous solution, w/w). The mixture was stirred at room temperature for 4 hours, after which it was heated to reflux for an additional 24 hours. The flask was then cooled to room temperature and found to contain 3350 mL of clear liquid.

Poly(allylamine) crosslinked with epichlorohydrin prepared as described in Example 4 (30 g) was suspended in the clear liquid (2 L) and stirred for 10 minutes. Sodium hydroxide (20 g) was then added and the mixture stirred until it had dissolved. Next, the mixture was refluxed with stirring for 24 hours, cooled to room temperature, and the solid filtered off. The solid was then washed successively with methanol (one time using 10 L), sodium chloride (two times using 10 L of a 1M solution each time), water (three times using 10 L each time), and isopropanol (one time using 5 L). Vacuum drying afforded 35.3 g of dialkylated product.

24. Alkylation of Poly(allylamine) crosslinked with epichlorohydrin with (10-bromodecyl)trimethylammonium bromide and 1-bromodecane alkylating agents Poly(allylamine) crosslinked with epichlorohydrin prepared as described in Example 4 (10 g) was suspended in methanol (300 mL). Sodium hydroxide (4.99 g) was added and the mixture stirred until it dissolved. (10-bromodecyl) trimethylammonium bromide prepared as described in Example 22 (20.7 g) and 1-bromodecane were added and the mixture was refluxed with stirring for 20 hours. The mixture was then cooled to room temperature and washed successively with methanol (two times using 1 L each time), sodium chloride (two times using 1 L of a 1M solution each time), water (three times using 1 L each time), and isopropanol (one time using 1 L). Vacuum drying yielded 10.8 g of dialkylated product.

Dialkylated products were also prepared in analogous fashion using different amounts of 1-bromodecane as follows: (a) 3.19 g 1-bromodecane and 4.14 g sodium hydroxide to yield 11.8 g of dialkylated product; (b) 38.4 g 1-bromodecane and 6.96 g sodium hydroxide to yield 19.1 g of dialkylated product.

Dialkylated products were also prepared in analogous fashion using the following combinations of alkylating agents: 1-bromodecane and (4-bromobutyl) trimethylammonium bromide; 1-bromodecane and (6-bromohexyl)trimethylammonium bromide; 1-bromodecane and (8-bromooctyl)trimethylammonium bromide; 1-bromodecane and (2-bromoethyl) trimethylammonium bromide; 1-bromodecane and (3-bromopropyl)trimethylammonium bromide; 1-bromohexane and (6-bromohexyl)trimethylammonium bromide; 1-bromododecane and (12-bromododecyl) trimethylammonium bromide; and 1-bromooctane and (6-bromohexyl) trimethylammonium bromide.

25. Alkylation of Poly(allylamine) crosslinked with epichlorohydrin with 11-bromo-1-undecanol alkylating agent Poly(allylamine) crosslinked with epichlorohydrin prepared as described in Example 4 (5.35 g) was suspended in methanol (100 mL). Sodium hydroxide (1.10 g) was added and the mixture stirred until it dissolved. 11-bromo-1-undecanol (5.0 g) was added and the mixture was refluxed with stirring for 20 hours, after which it was cooled to room temperature and washed successively with methanol (one time using 3 L), sodium chloride (two times using 500 mL of a 1M solution each time), and water (three times using 1 L each time). Vacuum drying yielded 6.47 g of alkylated product.

The reaction was also performed using 1.05 g sodium hydroxide and 10 g 11-bromo-1-undecanol to yield 8.86 g of alkylated product.

26. Alkylation of Poly(allylamine) crosslinked with epichlorohydrin with N-(2,3-epoxy propane)butyramide alkylating agent The first step is the preparation of N-allyl butyramide as follows.

Butyroyl chloride (194.7 g, 1.83 mol) in 1 L of tetrahydrofuran was added to a three neck round bottom flask equipped with a thermometer, stir bar, and dropping funnel. The contents of the flask were then cooled to 15° C. in an ice bath while stirring. Allylamine (208.7 g, 3.65 mol) in 50 mL of tetrahydrofuran was then added slowly through the dropping funnel while maintaining stirring. Throughout the addition, the temperature was maintained at 15° C. After addition was complete, stirring continued for an additional 15 minutes, after which the solid allylamine chloride precipitate was filtered off. The filtrate was concentrated under vacuum to yield 236.4 g of N-allyl butyramide as a colorless viscous liquid.

N-allyl butyramide (12.7 g, 0.1 mol) was taken into a 1 L round bottom flask equipped with a stir bar and air condenser. Methylene chloride (200 mL) was added to the flask, followed by 3-chloroperoxybenzoic acid (50–60% strength, 200 g) in five portions over the course of 30 minutes and the reaction allowed to proceed. After 16 hours, TLC analysis (using 5% methanol in dichloromethane) showed complete formation of product. The reaction mixture was then cooled and filtered to remove solid benzoic acid precipitate. The filtrate was washed with saturated sodium sulfite solution (two times using 100 mL each time) and then with saturated sodium bicarbonate solution (two times using 100 mL each time). The dichloromethane layer was then dried with anhydrous sodium sulfate and concentrated under vacuum to yield 10.0 g of N-(2,3-epoxypropane) butyramide as a light yellow viscous liquid.

Poly(allylamine) crosslinked with epichlorohydrin prepared as described in Example 4 (10 g, −80 sieved) and methanol (250 mL) were added to a 1 L round bottom flask, followed by N-(2,3-epoxypropane) butyramide (0.97 g, 0.0067 mol, 5 mol %) and then sodium hydroxide pellets (0.55 g, 0.01375 mol). The mixture was stirred overnight at room temperature. After 16 hours, the reaction mixture was filtered and the solid washed successively with methanol (three times using 300 mL each time), water (two times using 300 mL each time), and isopropanol (three times using 300 mL each time. Vacuum drying at 54° C. overnight yielded 9.0 g of the alkylated product as a light yellow powder.

Alkylated products based upon 10 mol %, 20 mol %, and 30 mol % N-(2,3-epoxypropane) butyramide were prepared in analogous fashion except that 9a) in the 10 mol % case, 1.93 g (0.013 mol) N-(2,3-epoxypropane) butyramide and 1.1 g (0.0275 mol) sodium hydroxide pellets were used to yield 8.3 g of alkylated product, (b) in the 20 mol % case, 3.86 g (0.026 mol) N-(2,3-epoxypropane) butyramide and 2.1 g (0.053 mol) sodium hydroxide pellets were used to yield 8.2 g of alkylated product, and (c) in the 30 mol % case. 5.72 g (0.04 mol) N-(2,3-epoxypropane) butyramide and 2.1 g (0.053 mol) sodium hydroxide pellets were used to yield 8.32 g of alkylated product.

27. Alkylation of Poly(allylamine) crosslinked with epichlorohydrin with N-(2,3-epoxypropane) hexanamide alkylating agent The first step is the preparation of N-allyl hexanamide as follows.

Hexanoyl chloride (33 g, 0.25 mol) in 250 mL of tetrahydrofuran was added to a three neck round bottom flask equipped with a thermometer, stir bar, and dropping funnel. The contents of the flask were then cooled to 15° C. in an ice bath while stirring. Allylamine (28.6 g, 0.5 mol) in 200 mL of tetrahydrofuran was then added slowly through the dropping funnel while maintaining stirring. Throughout the addition, the temperature was maintained at 15° C. After addition was complete, stirring continued for an additional 15 minutes, after which the solid allylamine chloride precipitate was filtered off. The filtration was concentrated under vacuum to yield 37 g of N-allyl hexanamide as a colorless viscous liquid.

N-allyl hexanamide (16 g, 0.1 mol) was taken into a 1 L round bottom flask equipped with a stir bar and air condenser. Methylene chloride (200 mL) was added to the flask, followed by 3-chloroperoxybenzoic acid (50–60% strength, 200 g) in five portions over the course of 30 minutes and the reaction allowed to proceed. After 16 hours, TLC analysis (using 5% methanol in dichloromethane) showed complete formation of product. The reaction mixture was then cooled and filtered to remove solid enzoic acid precipitate. The filtrate was washed with saturated sodium sulfite solution (two times using 100 mL each time) and then with saturated sodium bicarbonate solution (two times using 100 mL each time). The dichloromethane layer was then dried with anhydrous sodium sulfate and concentrated under vacuum to yield 14.2 g of N-(2,3-epoxypropane) hexanamide as a light yellow viscous liquid.

Poly(allylamine) crosslinked with epichlorohydrin prepared as described in Example 4 (10 g, –80 sieved) and methanol (250 mL) were added to a 1 L round bottom flask, followed by N-(2,3-epoxypropane) hexanamide (4.46 g, 0.026 mol, 20 mol %) and then sodium hydroxide pellets (2.1 g, 0.053 mol). The mixture was stirred overnight at room temperature. After 16 hours, the reaction mixture was filtered and the solid washed successively with methanol (three times using 300 mL each time), water (two times using 300 mL each time), and isopropanol (three times using 300 mL each time. Vacuum drying at 54° C. overnight yielded 9.59 g of the alkylated product as a light yellow powder.

An alkylated product based upon 30 mol % N-(2,3-epoxypropane) hexanamide was prepared in analogous fashion except that 6.84 g (0.04 mol) N-(2,3-epoxypropane) hexanamide was used to yield 9.83 g of alkylated product.

28. Alkylation of Poly(allylamine) crosslinked with epichlorohydrin with (6-Bromohexyl)trimethylammonium bromide and 1-bromodecane alkylating agent To a 12-1 round bottom flask equipped with a mechanical stirrer, a thermometer, and a condenser is added methanol (5 L) and sodium hydroxide (133.7 g). The mixture is stirred until the solid has dissolved and crosslinked poly (allylamine) (297 g; ground to –80 mesh size) is added along with additional methanol (3 L). (6-Bromohexyl) trimethylammonium bromide (522.1 g) and 1-bromodecane (311.7 g) are added and the mixture heated to 65° C. with stirring. After 18 hours at 65° C. the mixture is allowed to cool to room temperature. The solid is filtered off and rinsed by suspending, stirring for 30 minutes, and filtering off the solid from: methanol, 12 L; methanol, 12 L; 2M aqueous NaCl, 22 L; 2M aqueous NaCl, 22 L; deionized water, 22 L; deionized water, 22 L; deionized water, 22 L and isopropanol, 22 L. The solid is dried in a vacuum oven at 50° C. to yield 505.1 g of off-white solid. the solid is then ground to pass through an 80 mesh sieve.

Testing of Polymers

Preparation of Artificial Intestinal Fluid

Sodium carbonate (1.27 g) and sodium chloride (1.87 g) were dissolved in 400 mL of distilled water. To this solution was added either glycocholic acid (1.95 g, 4.0 mmol) or glycochenodeoxycholic acid (1.89 g, 4.0 mmol) to make a 10 mM solution. The pH of the solution was adjusted to 6.8 with acetic acid. These solutions were used for the testing of the various polymers.

Polymers were tested as follows.

To a 14 mL centrifuge tube was added 10 mg of polymer and 10 mL of a bile salt solution in concentrations ranging from 0.1–10 mM prepared from 10 mM stock solution (prepared as previously described) and buffer without bile salt, in the appropriate amount. The mixture was stirred in a water bath maintained at 37° C. for three hours. The mixture was then filtered. The filtrate was analyzed for total 3-hydroxy steroid content by an enzymatic assay using 3a-hydroxy steroid dehydrogenase, as described below.

Enzymatic Assay for Total Bile Salt Content

Four stock solutions were prepared.

Solution 1—Tris-HCl buffer, containing 0.133M Tris, 0.666 mM EDTA at pH 9.5.

Solution 2—Hydrazine hydrate solution, containing 1M hydrazine hydrate at pH 9.5.

Solution 3—NAD solution, containing 7 mM NAD+ at pH 7.0.

Solution 4—HSD solution, containing 2 units/mL in Tris-HCl buffer (0.03M Tris, 1 mM EDTA) at pH 7.2.

To a 3 mL cuvette was added 1.5 mL of Solution 1, 1.0 mL of Solution 2, 0.3 mL of solution 3, 0.1 mL of Solution 4 and 0.1 mL of supernatant/filtrate from a polymer test as described above. The solution was placed in a UV-VIS spectrophotometer and the absorbance (O.D.) of NADH at 350 nm was measured. The bile salt concentration was determined from a calibration curve prepared from dilutions of the artificial intestinal fluid prepared as described above.

All of the polymers previously described were tested in the above manner and all were efficacious in removing bile salts from the artificial intestinal fluid.

Use

The polymers according to the invention may be administered orally to a patient in a dosage of about 1 mg/kg/day to about 10 g/kg/day; the particular dosage will depend on the individual patient (e.g., the patient's weight and the extent of bile salt removal required). The polymer may be administrated either in hydrated or dehydrated form, and may be flavored or added to a food or drink, if desired to enhance patient acceptability. Additional ingredients such as other bile acid sequestrants, drugs for treating hypercholesterolemia, atherosclerosis or other related indications, or inert ingredients, such as artificial coloring agents may be added as well.

Examples of suitable forms for administration include pills, tablets, capsules, and powders (e.g., for sprinkling on food). The pill, tablet, capsule, or powder can be coated with a substance capable of protecting the composition from the gastric acid in the patient's stomach for a period of time sufficient to allow the composition to pass undisintegrated into the patient's small intestine. The polymer may be administered alone or in combination with a pharmaceutically acceptable carrier substance, e.g., magnesium carbonate, lactose, or a phospholipid with which the polymer can form a micelle.

EQUIVALENTS

Those skilled in the art will know, or be able to ascertain, using no more than routine experimentation, many equivalents to the specific embodiments of the invention described herein. These and all other equivalents are intended to be encompassed by the following claims.

What is claimed is:

1. An alkylated crosslinked polymer comprising the reaction product of:
   a) one or more crosslinked polymers, salts or copolymers thereof characterized by a repeat unit selected from the group consisting of:

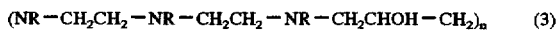

where n is a positive integer and each R, independently, is H or a $C_1$–$C_8$ alkyl group; and
   b) at least one aliphatic alkylating agent, said reaction product characterized in that:
      (i) at least some of the nitrogen atoms in said repeat units are unreacted with said alkylating agent; and
      (ii) less than 10 mol % of the nitrogen atoms in said repeat units that react with said alkylating agent form quaternary ammonium units.

2. An alkylated crosslinked polymer comprising the reaction product of:
   a) one or more crosslinked polymers, salts or copolymers thereof characterized by a repeat unit having the formula

where n is a positive integer and each R, independently, is H or a $C_1$–$C_8$ alkyl group; and
   b) at least one aliphatic alkylating agent, said reaction product characterized in that:
      (i) at least some of the nitrogen atoms in said repeat units are unreacted with said alkylating agent; and
      (ii) less than 10 mol % of the nitrogen atoms in said repeat units that react with said alkylating agent form quaternary ammonium units.

3. The polymer of claim 2 wherein said polymer is crosslinked by means of a multifunctional crosslinking agent, said agent being present in an amount from about 0.5–25% by weight, based upon the combined weight of monomer and crosslinking agent.

4. The polymer of claim 2 wherein said crosslinking agent is present in an amount from about 2.5–20% by weight, based upon the combined weight of monomer and crosslinking agent.

5. The polymer of claim 2 wherein said crosslinking agent comprises epichlorohydrin.

6. The polymer of claim 2 wherein said polymer, salt or copolymer thereof is characterized by a repeat unit having the formula

7. The polymer of claim 2 wherein said alkylating agent has the formula RX where R is a $C_1$–$C_{20}$ alkyl, $C_1$–$C_{20}$ hydroxyalkyl, $C_1$–$C_{20}$ alkylammonium, or $C_1$–$C_{20}$ alkylamido group and X is one or more electrophilic leaving groups.

8. The polymer of claim 7 wherein X is a halide, epoxy, tosylate, or mesylate.

9. The polymer of claim 2 wherein said polymer is reacted with at least two of said alkylating agent, one of said alkylating agents has the formula RX where R is a $C_1$–$C_{20}$ alkyl group and X is one or more electrophilic leaving groups, and the other of said alkylating agents has the formula R'X where R' is a $C_1$–$C_{20}$ alkyl ammonium group and X is one or more electrophilic leaving groups.

10. The polymer of claim 9 wherein one of said alkylating agents having the formula RX is an alkyl halide and the other of said alkylating agents having the formula R'X is an alkyl halide ammonium salt.

11. The polymer of claim 10 wherein said alkyl halide is a $C_4$–$C_{20}$ alkyl halide and said alkyl halide ammonium salt is a $C_4$–$C_{18}$ alkyl halide ammonium salt.

12. The polymer of claim 10 wherein said alkyl halide is a $C_{10}$ alkyl halide and said alkyl halide ammonium salt is a $C_6$ alkyl halide ammonium salt.

13. The polymer of claim 2 wherein said polymer is reacted with at least two of said alkylating agent, one of said alkylating agents has the formula RX where R is a $C_1$–$C_{20}$ alkyl group and X is one or more electrophilic leaving groups, and the other of said alkylating agents has the formula R'X where R' is a $C_1$–$C_{20}$ hydroxyalkyl group and X is one or more electrophilic leaving groups.

14. The polymer of claim 13 wherein one of said alkylating agents is an alkyl halide and the other of said alkylating agents is a hydroxy alkyl halide.

15. The polymer of claim 2 wherein said polymer is reacted with at least two of said alkylating agent, one of said alkylating agents is a $C_1$–$C_{20}$ dihaloalkane and the other of said alkylating agents is a $C_1$–$C_{20}$ alkylammonium salt.

16. The polymer of claim 1 wherein said alkylating agent comprises a $C_1$–$C_{20}$ alkyl halide.

17. The polymer of claim 16 wherein said alkyl halide is a $C_4$–$C_{18}$ alkyl halide.

18. The polymer of claim 1 wherein said alkylating agent comprises a $C_1$–$C_{20}$ dihaloalkane.

19. The polymer of claim 18 wherein said dihaloalkane is a 1,10-dihalodecane.

20. The polymer of claim 1 wherein said alkylating agent comprises a $C_1$–$C_{20}$ hydroxyalkyl halide.

21. The polymer of claim 20 wherein said hydroxyalkyl halide is an 11-halo-1-undecanol.

22. The polymer of claim 1 wherein said alkylating agent comprises a $C_1$–$C_{20}$ alkyl halide ammonium salt.

23. The polymer of claim 22 wherein said alkyl halide ammonium salt is a $C_4$–$C_{12}$ haloalkyl trimethylammonium salt.

24. The method of claim 1 wherein said alkylating agent comprises a $C_1$–$C_{20}$ alkyl epoxy ammonium salt.

25. The polymer of claim 24 wherein said alkyl epoxy ammonium salt is a (glycidylpropyl)trimethylammonium salt.

26. The polymer of claim 1 wherein said alkylating agent comprises a $C_1$–$C_{20}$ epoxy alkylamide.

27. The polymer of claim 26 wherein said epoxy alkylamide is selected from the group consisting of N-(2,3-epoxypropane)butyramide, N-(2,3-epoxypropane)hexanamide, and combinations thereof.

28. The polymer of claim 1 wherein said polymer is reacted with at least two of said alkylating agent, one of said alkylating agents has the formula RX where R is a $C_1$–$C_{20}$ alkyl group and X is one or more electrophilic leaving groups, and the other of said alkylating agents has the formula R'X where R' is a $C_1$–$C_{20}$ alkyl ammonium group and X is one or more electrophilic leaving groups.

29. The polymer of claim 28 wherein one of said alkylating agents is an alkyl halide and the other of said alkylating agents is an alkyl halide ammonium salt.

30. The polymer of claim 29 wherein said alkyl halide is a $C_4$–$C_{20}$ alkyl halide and said alkyl halide ammonium salt is a $C_4$–$C_{18}$ alkyl halide ammonium salt.

31. The polymer of claim 29 wherein said alkyl halide is a $C_{10}$ alkyl halide and said alkyl halide ammonium salt is a $C_6$ alkyl halide ammonium salt.

32. The polymer of claim 1 wherein said polymer is reacted with at least two of said alkylating agent, one of said alkylating agents has the formula RX where R is a $C_1$–$C_{20}$ alkyl group and X is one or more electrophilic leaving groups, and the other of said alkylating agents has the formula R'X where R' is a $C_1$–$C_{20}$ hydroxyalkyl group and X is one or more electrophilic leaving groups.

33. The polymer of claim 32 wherein one of said alkylating agents is an alkyl halide and the other of said alkylating agents is a hydroxyalkyl halide.

34. The polymer of claim 1 wherein said polymer is reacted with at least two of said alkylating agent, one of said alkylating agents is a $C_1$–$C_{20}$ dihaloalkane and the other of said alkylating agents is a $C_1$–$C_{20}$ alkylammonium salt.

35. The polymer of claim 6 wherein said polymer is reacted with at least two of said alkylating agent, one of said alkylating agents is a $C_{10}$ alkyl halide and the other of said alkylating agents is a $C_6$ alkyl halide ammonium salt.

36. An alkylated crosslinked polymer comprising the reaction product of:

a) one or more crosslinked polymers, salts or copolymers thereof characterized by a repeat unit selected from the group consisting of:

  (1)

  (2)

  (3)

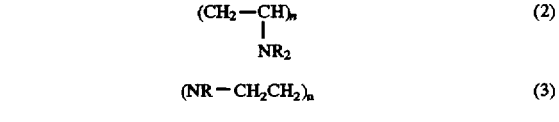  (4)

where n is a positive integer and each R, independently, is H or a $C_1$–$C_8$ alkyl group; and b) at least one aliphatic alkylating agent, said reaction product characterized in that:

(i) at least some of the nitrogen atoms in said repeat units are unreacted with said alkylating agent;

(ii) less than 10 mol % of the nitrogen atoms in said repeat units that react with said alkylating agent form quaternary ammonium units; and (iii) said polymer is crosslinked by means of a multifunctional crosslinking agent, said agent being present in an amount from 1–10% by weight based upon the combined weight of monomer and crosslinking agent.

37. An alkylated crosslinked polymer comprising the reaction product of:

a) one or more crosslinked polymers, salts or copolymers thereof characterized by a repeat unit selected from the group consisting of:

  (1)

  (2)

  (3)

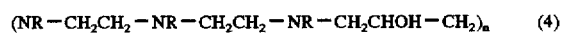  (4)

where n is a positive integer and each R, independently, is H or a $C_1$–$C_8$ alkyl group; and b) at least one hydrophobic aliphatic alkylating agent, said reaction product characterized in that:

(i) at least some of the nitrogen atoms in said repeat units are unreacted with said alkylating agent; and (ii) less than 10 mol % of the nitrogen atoms in said repeat units that react with said alkylating agent form quaternary ammonium units.

38. An alkylated crosslinked polymer comprising the reaction product of:

a) one or more crosslinked polymers, salts or copolymers thereof characterized by a repeat unit selected from the group consisting of:

  (1)

  (2)

  (3)

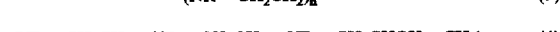  (4)

where n is a positive integer and each R, independently, is H or a $C_1$–$C_8$ alkyl group; and b) at least one alkylating agent, having the formula RX wherein R is a $C_1$–$C_{20}$ alkylammonium group and X is an electrophilic leaving group, said reaction product characterized in that:

(i) at least some of the nitrogen atoms in said repeat units are unreacted with said alkylating agent; and (ii) less than 10 mol % of the nitrogen atoms in said repeat units that react with said alkylating agent form quaternary ammonium units.

* * * * *